United States Patent

Fitzgerald

[11] Patent Number: 5,163,561
[45] Date of Patent: Nov. 17, 1992

[54] DENTAL CLEANING KIT

[76] Inventor: Linda M. Fitzgerald, 7590 Crossbill Cir., Rapid City, S. Dak. 57702

[21] Appl. No.: 835,518

[22] Filed: Feb. 14, 1992

[51] Int. Cl.⁵ .......................... A46B 7/04; B65D 83/00
[52] U.S. Cl. ............................... 206/581; 206/362.1; 206/369; 206/374; 15/145
[58] Field of Search ...................... 206/581, 362.1, 369, 206/374; 15/145

[56] References Cited

U.S. PATENT DOCUMENTS

| 390,089 | 9/1888 | McClelland | 206/581 X |
| 3,256,031 | 6/1966 | Fillweber | 15/145 |
| 4,598,437 | 7/1986 | Ernest et al. | 15/145 X |
| 4,811,445 | 3/1989 | Liagieski et al. | 15/145 |
| 4,890,732 | 1/1990 | Shackelford | 15/14.5 X |
| 4,913,282 | 4/1990 | Didier | 206/581 X |

FOREIGN PATENT DOCUMENTS 216355 5/1924 United Kingdom ................. 15/145

Primary Examiner—William I. Price
Attorney, Agent, or Firm—Leon Gilden

[57] ABSTRACT

A dental cleaning kit includes a housing arranged with a cavity directed therethrough, with a trough positioned in communication with the cavity at a lower distal end of the front wall and floor of the housing to accommodate a plurality of replaceable toothbrush heads thereon. A side wall of the housing includes a handle structure to receive in a selective manner cleaning components to include a toothpick head and a dental floss holder head. A modification of the invention includes a mirror handle and mirror mounted to the side wall within a loop structure, as well as a further mirror member mounted to a deformable goose neck conduit secured to the first side wall to permit ease of visual observation by an individual during use of the apparatus.

8 Claims, 4 Drawing Sheets

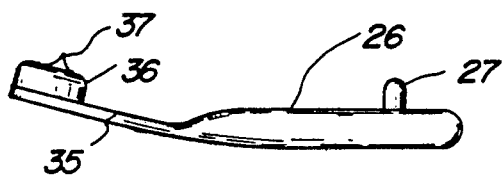
FIG. 5
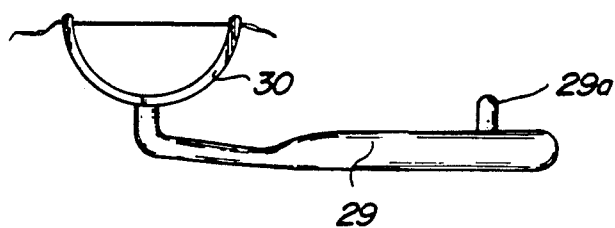
FIG. 6
FIG. 7
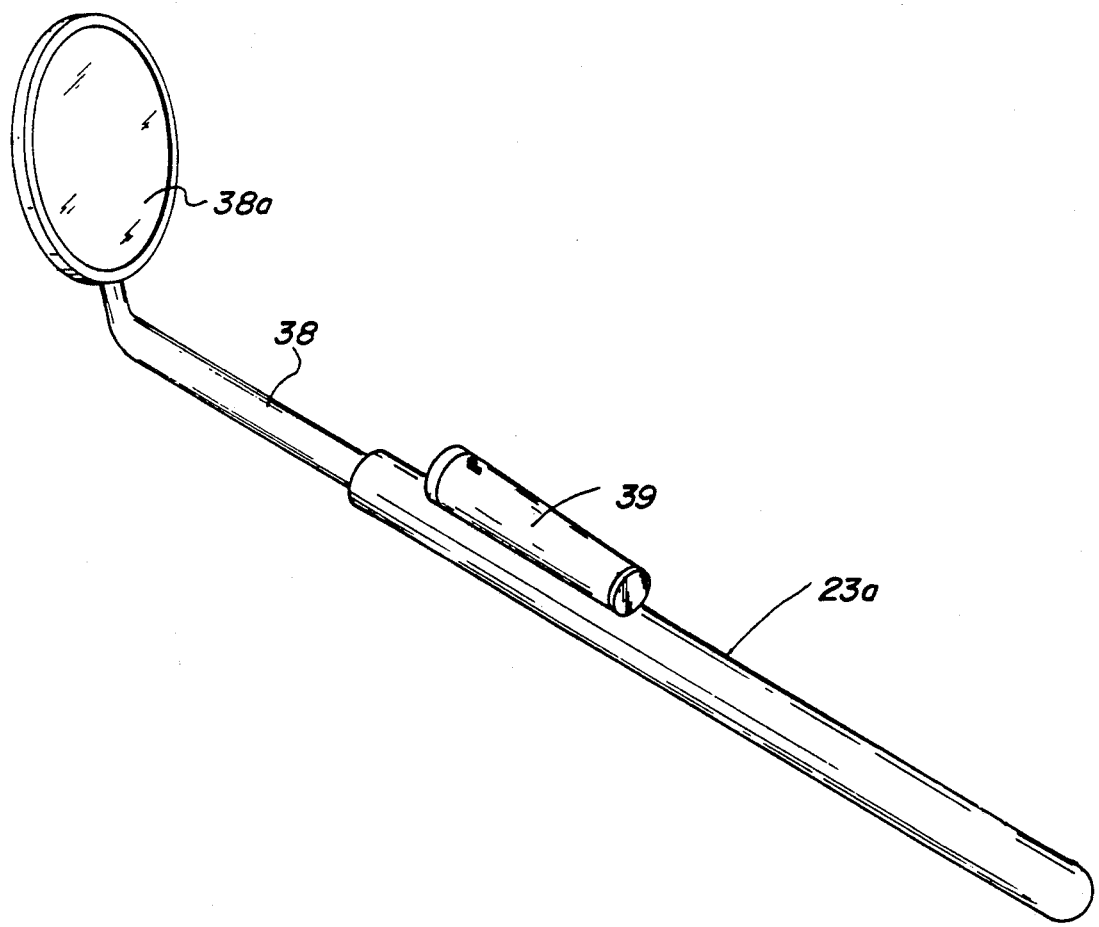

DENTAL CLEANING KIT

BACKGROUND OF THE INVENTION

1. Field of the Invention

The field of invention relates to dental cleaning apparatus, and more particularly pertains to a new and improved dental cleaning kit wherein the same provides for an operative inter-relationship of various components for use in a dental cleaning procedure.

2. Description of the Prior Art

The sanitary use for replaceable head structure relative to a toothbrush apparatus has been presented in the prior art wherein the prior art has set forth in the U.S. Pat. No. 4,461,053 to Nitzsche a toothbrush handle including a replaceable head member slidably received within the handle.

U.S. Pat. No. 4,796,325 to Bortman sets forth an angularly adjustable doubled headed toothbrush structure providing for angular orientation of the toothbrush head relative to the toothbrush handle.

Accordingly, it may be appreciated that there continues to be a need for a new and improved dental cleaning kit as set forth by the instant invention which addresses both the problems of ease of use as well as effectiveness in construction in providing for an organization to accommodate various components for use in a dental cleaning procedure and in this respect, the present invention substantially fulfills this need.

SUMMARY OF THE INVENTION

In view of the foregoing disadvantages inherent in the known types of dental apparatus now present in the prior art, the present invention provides a dental cleaning kit wherein the same provides a housing mounting replaceable toothbrush heads to be utilized in association with a handle structure. As such, the general purpose of the present invention, which will be described subsequently in greater detail, is to provide a new and improved dental cleaning kit which has all the advantages of the prior art dental cleaning apparatus and none of the disadvantages.

To attain this, the present invention provides a dental cleaning kit including a housing arranged with a cavity directed therethrough, with a trough positioned in communication with the cavity at a lower distal end of the front wall and floor of the housing to accommodate a plurality of replaceable toothbrush heads thereon. A side wall of the housing includes a handle structure to receive in a selective manner cleaning components to include a toothpick head and a dental floss holder head. A modification of the invention includes a mirror handle and mirror mounted to the side wall within a loop structure, as well as a further mirror member mounted to a deformable goose neck conduit secured to the first side wall to permit ease of visual observation by an individual during use of the apparatus.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental cleaning kit which has all the advantages of the prior art dental cleaning apparatus and none of the disadvantages.

It is another object of the present invention to provide a new and improved dental cleaning kit which may be easily and efficiently manufactured and marketed.

It is a further object of the present invention to provide a new and improved dental cleaning kit which is of a durable and reliable construction.

An even further object of the present invention is to provide a new and improved dental cleaning kit which is susceptible of a low cost of manufacture with regard to both materials and labor, and which accordingly is then susceptible of low prices of sale to the consuming public, thereby making such dental cleaning kits enconomically available to the buying public.

Still yet another object of the present invention is to provide a new and improved dental cleaning kit which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an orthographic side view of the toothbrush structure utilized by the invention.

FIG. 6 is an orthographic side view of the dental floss cleaning head utilized by the invention.

FIG. 7 is an isometric illustration of a portable mirror structure utilized by the invention.

DESCRIPTION OF THE PREFERRED EMBODIMENT

Figure 1:
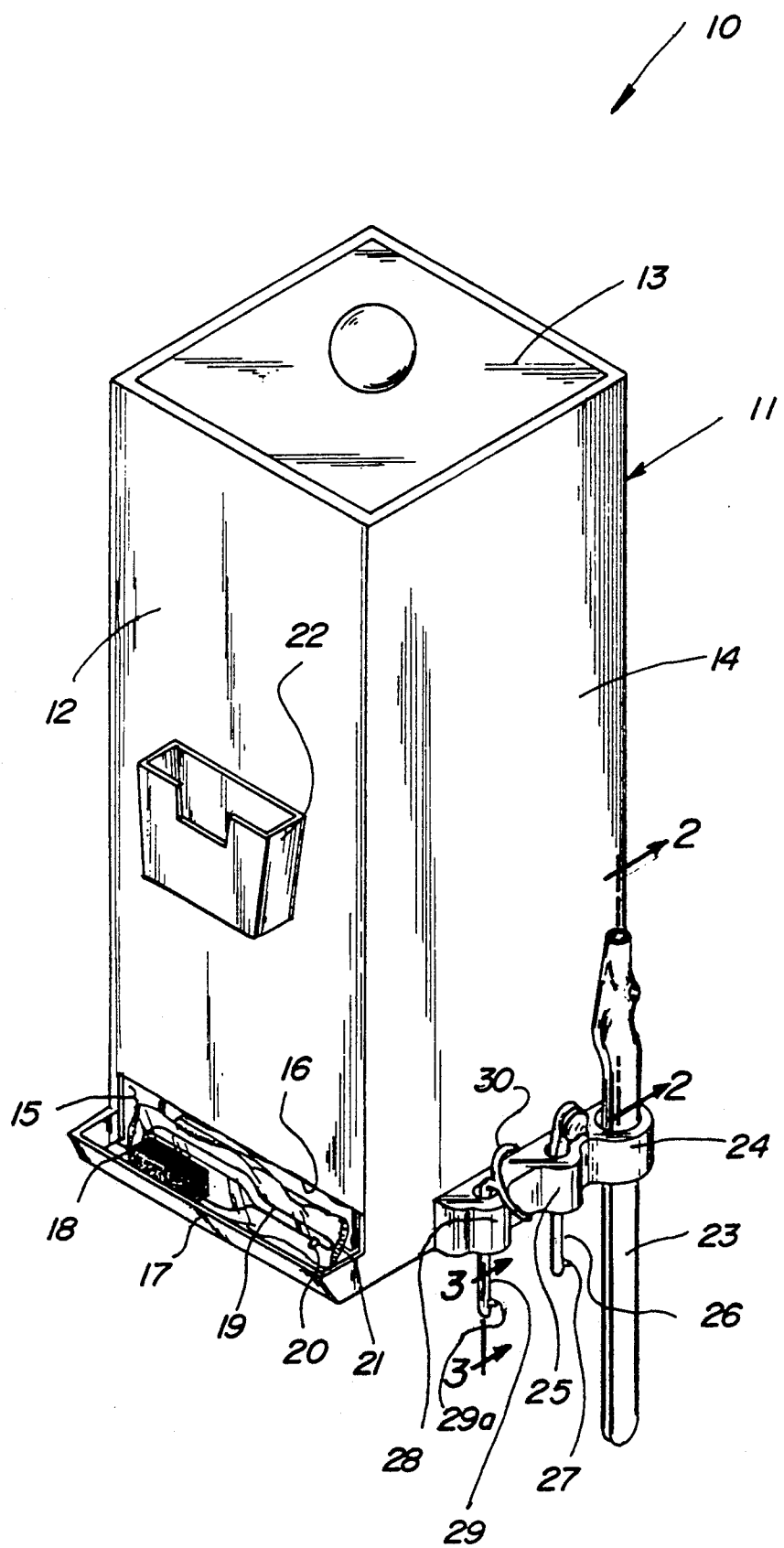
FIG. 1 is an isometric illustration of the instant invention.
Figure 2:
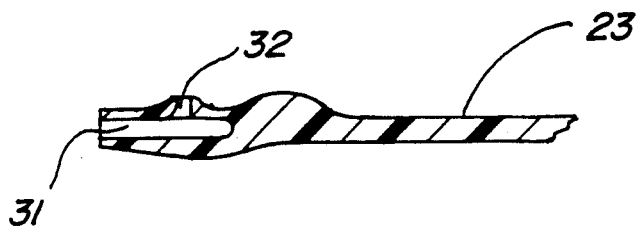
FIG. 2 is an orthographic view, taken along the lines 2—2 of FIG. 1 in the direction indicated by the arrows.

With reference now to the drawings, and in particular to FIGS. 1 to 8 thereof, a new and improved dental cleaning kit embodying the principles and concepts of the present invention and generally designated by the reference numeral 10 will be described.

More specifically, the dental cleaning kit 10 of the instant invention essentially comprises a housing 11, including a front wall 12 extending from a floor to an upper distal end, with the housing including a lid 13 securable to an upper distal end of the housing 11 above a housing cavity 15. The housing cavity 15 is accessed through a cavity opening 16 through the front wall 12 adjacent the housing floor, with a support trough 17 projecting orthogonally and forwardly of the floor, with the support trough 17 projecting beyond the front wall 12.

The first side wall 14 includes a plurality of support loops to include a first support loop 24, a second support loop 25, and a third support loop 28, as illustrated. A support handle 23 is received within the first support loop 24, with the support handle 23 including a support handle conduit 31 extending into the support handle from a forward distal end thereof intersecting a conduit detent receiving bore 32 adjacent a rear distal end of the conduit 31 within the support handle 23. One of a plurality of toothbrush heads 18 receivable from the support trough 17 that are stored within the housing cavity 15 is obtained by an individual in use, with an air and fluid impermeable covering sheath 21 arranged in surrounding relationship relative to each toothbrush 18 removed therefrom for securement to the support handle 23. Each toothbrush head 18 includes a toothbrush head body 19, with a body detent 20 orthogonally mounted relative to the body 19. The detent 20 is received within the detent receiving bore 32, in a manner to be described in more detail below. It should be further noted that a dental floss container 22 mounted to the front wall 12 is provided for the storage of dental floss therewithin as required for use as an alternative to the use of a dental floss support body 29 mounted within the third loop 28. The dental floss support body 29 includes a C-shaped floss support head 30, with a dental floss body detent 29a arranged for reception with the detent receiving bore 32. The second loop 25 includes a toothpick body 26 to include a toothpick body detent 27 received within the conduit detent receiving bore 32.

In this manner, selective heads are utilized relative to the support handle 23 in use.

Figure 3:
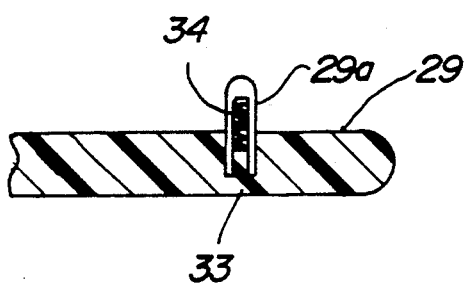
FIG. 3 is an orthographic view, taken along the lines 3—3 of FIG. 1 in the direction indicated by the arrows.
Figure 4:
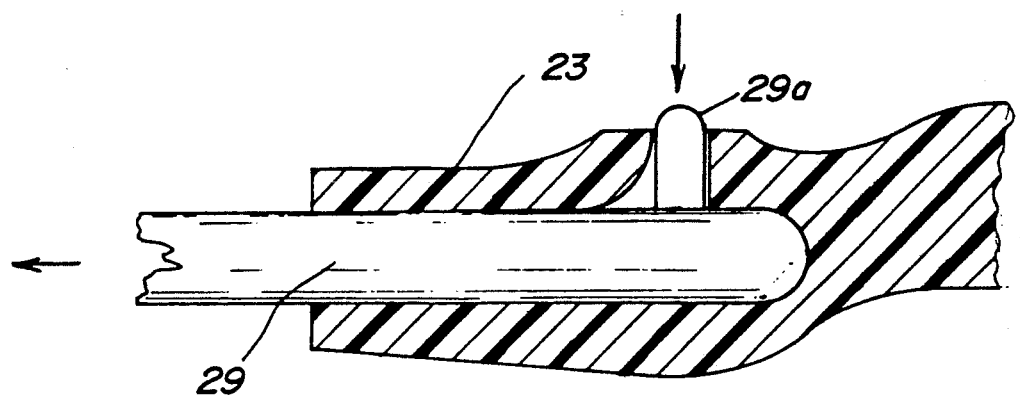
FIG. 4 is an enlarged orthographic cross-sectional illustration of a typical detent mounted within the support handle.

Each detent is constructed, in a manner such as illustrated in FIG. 3, to include a detent socket 33 mounting the detent projection 29a thereto. A detent spring 34 received within the detent projection maintains the detent in a biased projecting relationship relative to each body, such as illustrated in FIG. 3. In use, the detent projection is depressed in the detent socket against the detent spring 34 and projected within the support handle conduit 31 until the detent projection is received through the detent receiving bore 32 of the support handle 23.

The toothpick body 26 includes a toothpick body leg 35 oriented at a generally obtuse angle relative to the toothpick body (see FIG. 5), with a polymeric boss 36 mounted to the toothpick body leg, wherein the polymeric boss 36 includes a resilient polymeric projection 37 projecting medially of the polymeric boss 36 for use in the cleaning between adjacent tooth members within an individual.

The FIG. 7 illustrates the use a mirror leg 38 secured to a modified support handle 23a. A reflective mirror 38a is mounted at a forward distal end of the mirror leg 38 at an obtuse angle relative to the mirror leg, as illustrated. A flashlight member 39 is mounted to the modified support handle 23a adjacent the mirror leg 38 projecting towards the reflective mirror 38a for use in illumination of distal portions of an oral cleaning procedure.

Figure 8:
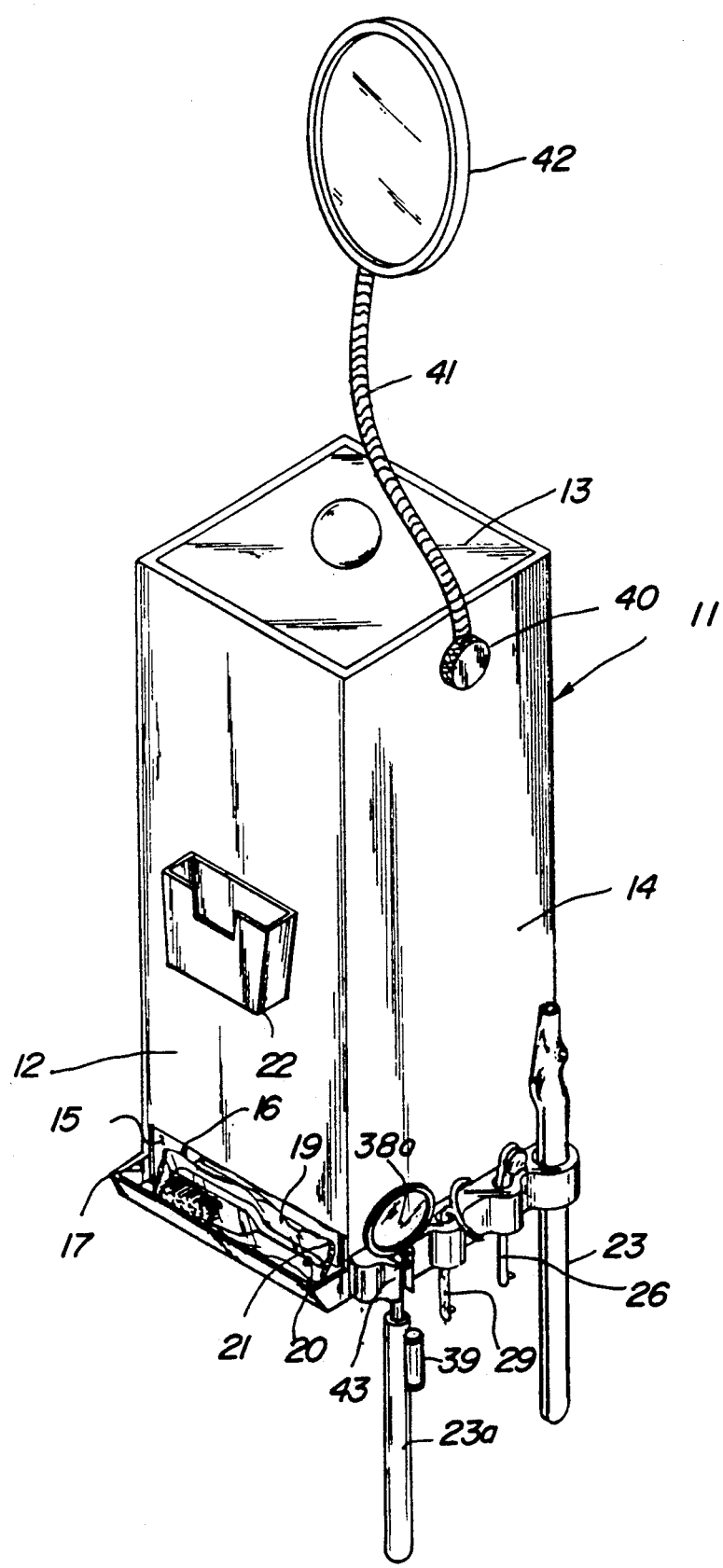
FIG. 8 is an isometric illustration of the modified housing incorporating the portable mirror structure of FIG. 7.

The FIG. 8 illustrates the use of the housing 11 to further include a spring clip 43 mounting the modified support handle 23a thereon. Further, a support boss 40 mounted to the first side wall adjacent the upper terminal end of the housing includes a deformable goose neck conduit 41 mounted fixedly at its lower distal end to the support boss 40. An upper distal end of the deformable goose neck conduit 41 includes a mirror member 42 mounted thereto for positioning the mirror member as required by an individual in use of the kit structure of the invention.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the United States is as follows:

1. A dental cleaning kit, comprising,
   a housing, the housing including a housing front wall, with the housing including spaced side walls, wherein the spaced side walls includes at least a first side wall and a housing floor, and a housing cavity defined within the housing between the side walls and the floor, and a lid securable to an upper distal end of the housing above the housing cavity, and a housing cavity opening directed through the housing front wall adjacent the floor, and a support trough projecting forwardly of the housing front wall from the floor, and the housing cavity including a plurality of toothbrush heads contained therewithin, each toothbrush head includes a toothbrush head body.

2. A dental cleaning kit as set forth in claim 1 including a first support loop, a second support loop, and a third support loop mounted to the first side wall, the first support loop including a support handle, the support handle including an elongate handle conduit directed into the support handle from a forward distal end of the support handle, and a detent receiving bore orthogonally intersecting the support handle conduit spaced from the support handle forward distal end, and said toothbrush head body receivable within said support handle conduit, and each toothbrush head body including a toothbrush head body detent, each toothbrush head body detent spring biased and projecting exteriorly of each toothbrush head body, wherein the toothbruch head body detent is receivable within the conduit detent receiving bore.

3. A dental cleaning kit as set forth in claim 2 wherein each toothbrush head and toothbrush head body is arranged in surrounding relationship relative to an air and fluid impermeable covering sheath.

4. A dental cleaning kit as set forth in claim 3 wherein the second support loop includes a toothpick body, the toothpick body including a toothpick body detent, the toothpick body detent spring biased within the toothpick body, and the toothpick body further including a polymeric boss mounted fixedly to the toothpick body spaced from the toothpick body detent, and the polymeric boss including a resilient polymeric projection projecting medially of the polymeric boss.

5. A dental cleaning kit as set forth in claim 4 wherein the third support loop includes a dental floss support body, the dental floss support body includes a dental floss support body detent spring biased within the dental floss support body, wherein the dental floss support body is arranged for reception within the support handle conduit, and the dental floss support body further including a C-shaped floss support head mounted to a forward distal end of the dental floss support body spaced from the dental floss support body detent.

6. A dental cleaning kit as set forth in claim 5 including a spring clip mounted to the first side wall adjacent the third support loop, wherein the spring clip includes a further support handle, the further support handle is arranged for reception within the spring clip and the further support handle including a mirror leg projecting longitudinally relative to the support handle and the reflective mirror mounted to a forward distal end of the mirror leg at an obtuse angle thereto.

7. A dental cleaning kit as set forth in claim 6 wherein the further support handle includes a flashlight member fixedly mounted to the support handle adjacent the mirror leg, the flashlight member aligned with the reflection mirror to effect selective illumination of the reflective mirror.

8. A dental cleaning kit as set forth in claim 7 including a support boss fixedly mounted to the first side wall adjacent an upper distal end of the first side wall, wherein the support boss includes a deformable goose neck conduit fixedly mounted at a first end of the goose neck conduit to the support boss, and a second end of the goose neck conduit mounted to a mirror member, the mirror member arranged for manual manipulation relative to the housing.

* * * * *